(12) United States Patent
Dziadik et al.

(10) Patent No.: US 7,367,983 B2
(45) Date of Patent: May 6, 2008

(54) VESSEL HARVESTING APPARATUS

(76) Inventors: Stephen P. Dziadik, 2553 Wye Oak La., Sarasota, FL (US) 34232; Thomas F. Kelly, 1880 Arlington St., Sarasota, FL (US) 34237

( * ) Notice: Subject to any disclaimer, the term of this patent is extended or adjusted under 35 U.S.C. 154(b) by 103 days.

(21) Appl. No.: 11/228,900

(22) Filed: Sep. 15, 2005

(65) Prior Publication Data

US 2007/0060938 A1 Mar. 15, 2007

(51) Int. Cl.
*A61B 17/32* (2006.01)

(52) U.S. Cl. ..................................... 606/170

(58) Field of Classification Search ................ 606/148, 606/159
See application file for complete search history.

(56) References Cited

U.S. PATENT DOCUMENTS

| | | | |
|---|---|---|---|
| 5,569,291 A | 10/1996 | Privitera et al. | |
| 5,695,514 A | 12/1997 | Chin | |
| 5,913,866 A | 6/1999 | Ginn et al. | |
| 6,004,335 A | 12/1999 | Vaitekunas et al. | |
| 6,007,551 A | 12/1999 | Peifer et al. | |
| 6,019,771 A | 2/2000 | Bennett et al. | |
| 6,022,313 A * | 2/2000 | Ginn et al. | 600/114 |
| 6,074,402 A | 6/2000 | Peifer et al. | |
| 6,080,102 A * | 6/2000 | Konou et al. | 600/114 |
| 6,099,535 A | 8/2000 | Lamport et al. | |
| 6,143,005 A | 11/2000 | Yoon et al. | |
| 6,149,659 A | 11/2000 | Ahmed | |
| 6,193,653 B1 | 2/2001 | Evans et al. | |
| 6,206,823 B1 | 3/2001 | Kolata et al. | |
| 6,214,028 B1 | 4/2001 | Yoon et al. | |
| 6,241,740 B1 | 6/2001 | Davis et al. | |
| 6,352,544 B1 | 3/2002 | Spitz | |
| 6,375,635 B1 | 4/2002 | Moutafis et al. | |
| 6,464,685 B1 | 10/2002 | Suzuki et al. | |
| 6,464,708 B1 | 10/2002 | Higuma et al. | |
| 6,527,786 B1 | 3/2003 | Davis et al. | |
| 6,610,072 B1 | 8/2003 | Christy et al. | |
| 6,632,228 B2 | 10/2003 | Fortier et al. | |
| 6,656,176 B2 | 12/2003 | Hess et al. | |
| 6,660,016 B2 | 12/2003 | Lindsay | |
| 6,679,892 B2 | 1/2004 | Guido et al. | |
| 6,685,713 B1 | 2/2004 | Ahmed | |
| 6,730,101 B1 | 5/2004 | Peifer et al. | |
| 6,818,003 B2 | 11/2004 | Genovesi | |
| 2003/0065349 A1 | 4/2003 | Hess et al. | |

(Continued)

*Primary Examiner*—Julian W. Woo
*Assistant Examiner*—Christina Gettman
(74) *Attorney, Agent, or Firm*—Charles J. Prescott

(57) ABSTRACT

A vessel harvesting apparatus including a shaft and a tip formed as a unit with, and positioned at a distal end of, the shaft. A handle is connected to a proximal end of the shaft for allowing an operator to feed and manipulate the tip. The tip defines a vessel receiving aperture extending longitudinally through the tip and being laterally offset from and generally parallel to a longitudinal axis of the shaft. The tip has a smooth, contoured outer surface narrowing toward the distal end thereof wherein the tip may be passed along and surrounding a vessel without substantial disruption of surrounding tissue. Transacting and ligating of the vessel positioned in the aperture and side branch vessels against the outer surface of the tip by dissection and/or cauterization is provided. The tip releases the vessel from surrounding tissue while being moved there along wherein the transfected portion of the vessel is more easily removed from surrounding tissue.

25 Claims, 8 Drawing Sheets

U.S. PATENT DOCUMENTS

| | | |
|---|---|---|
| 2004/0122458 A1 | 6/2004 | Opie et al. |
| 2004/0162462 A1* | 8/2004 | Knighton et al. ............. 600/36 |
| 2004/0204725 A1 | 10/2004 | Bayer |
| 2005/0004586 A1 | 1/2005 | Suval |
| 2005/0070940 A1 | 3/2005 | Genovesi |
| 2005/0096677 A1 | 5/2005 | Wellman et al. |

* cited by examiner

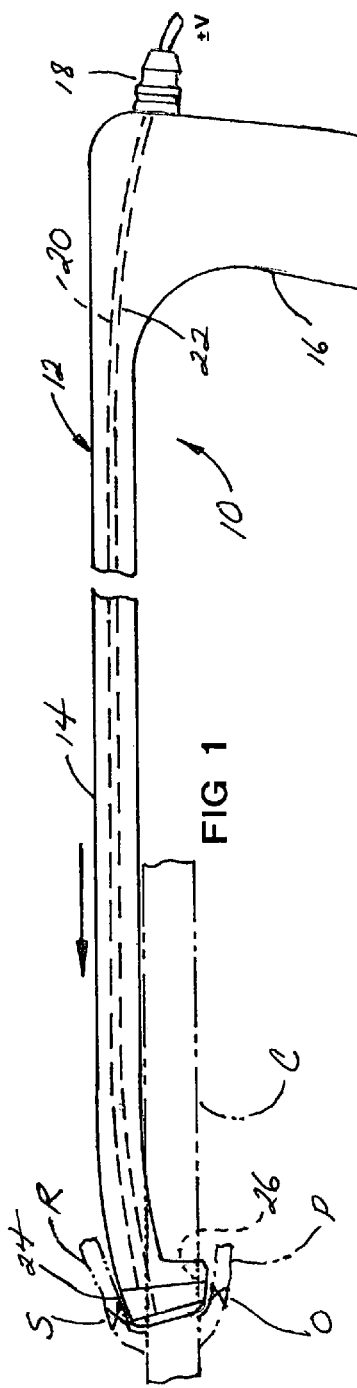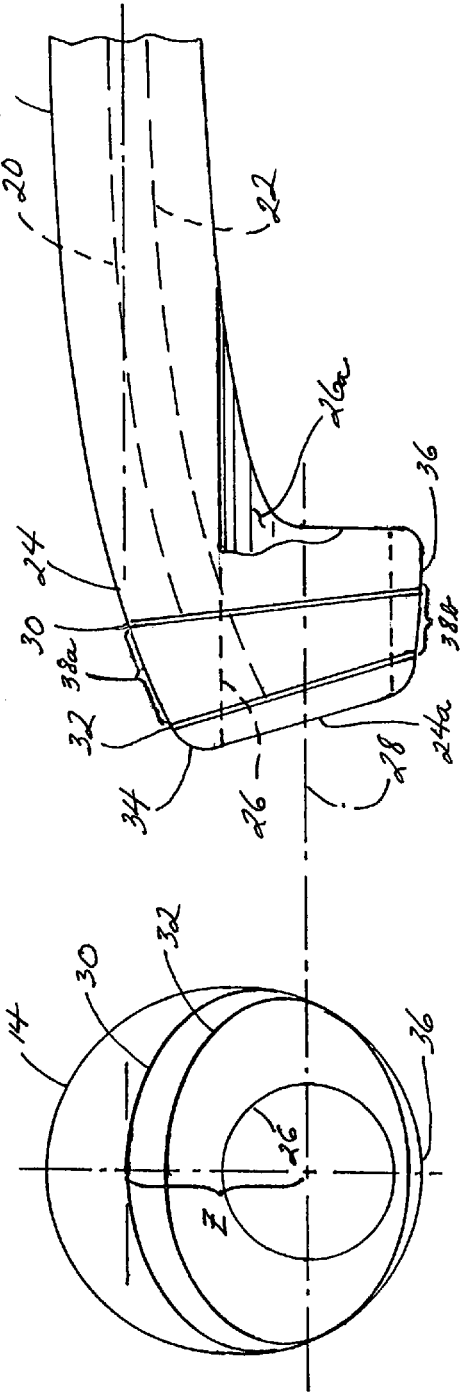

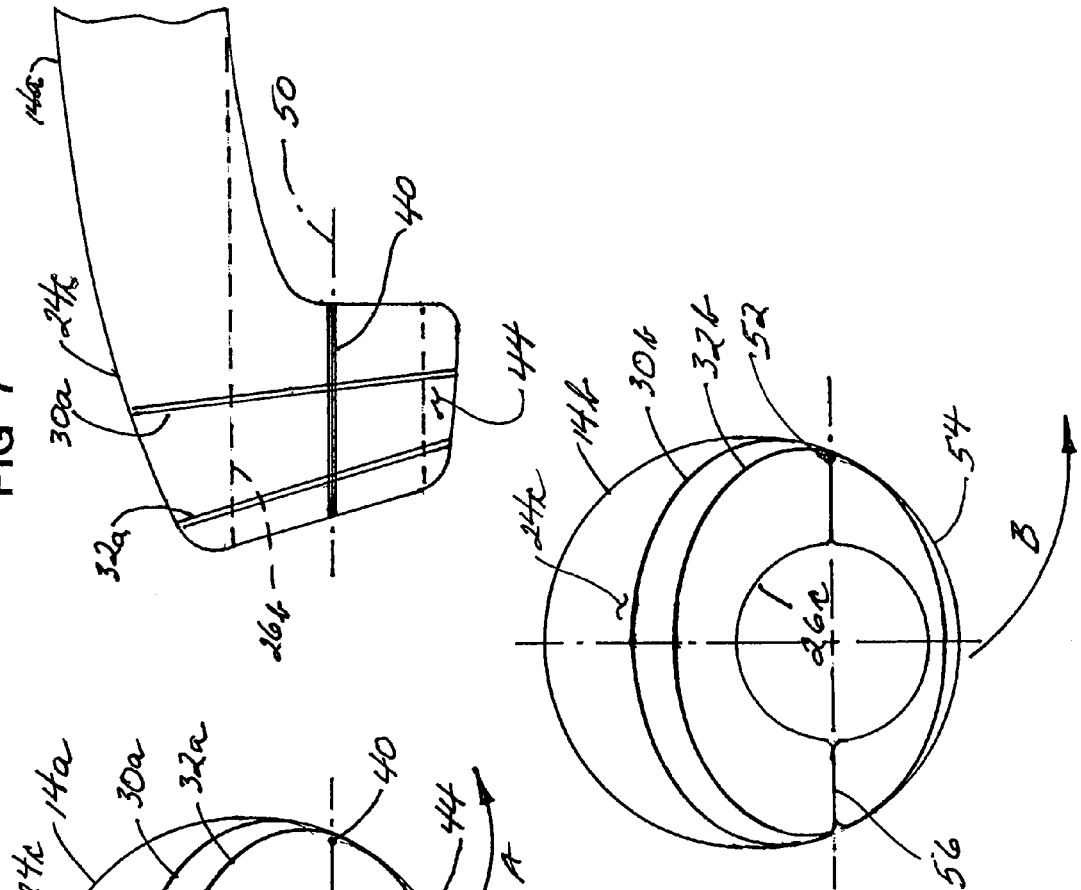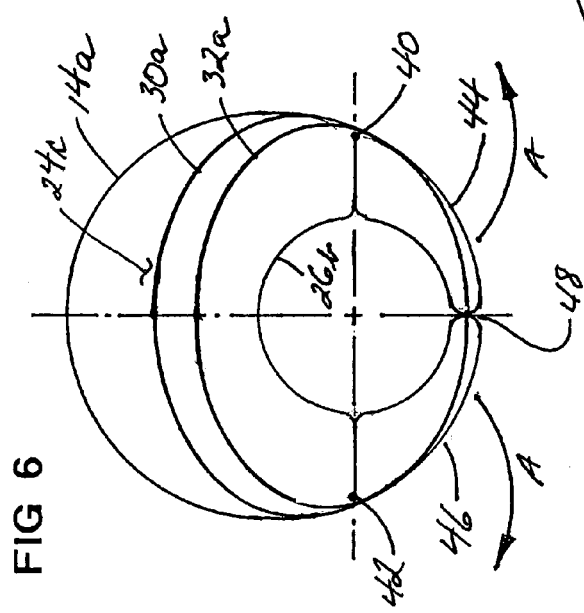

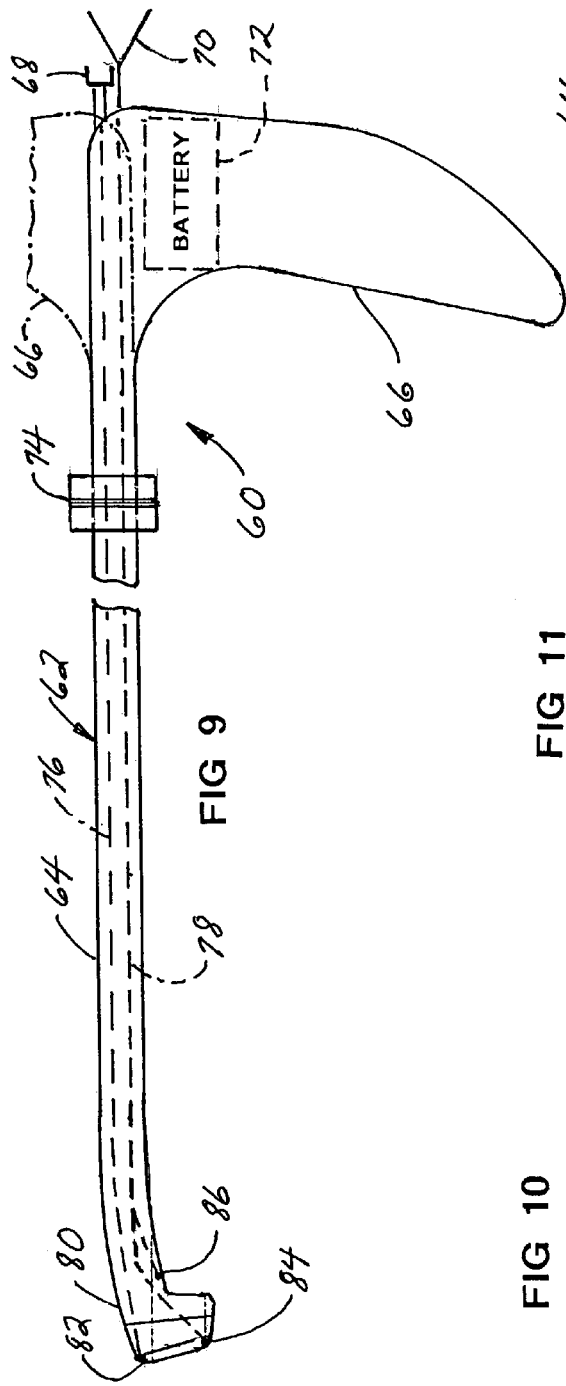
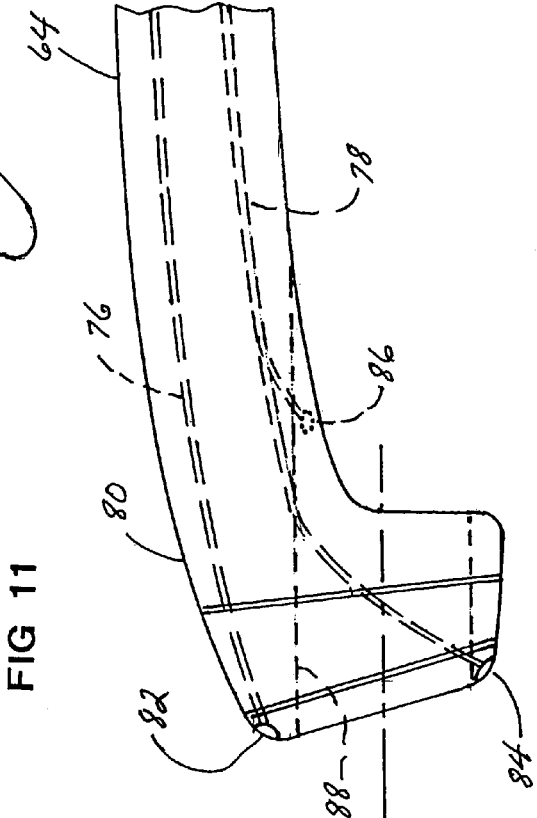
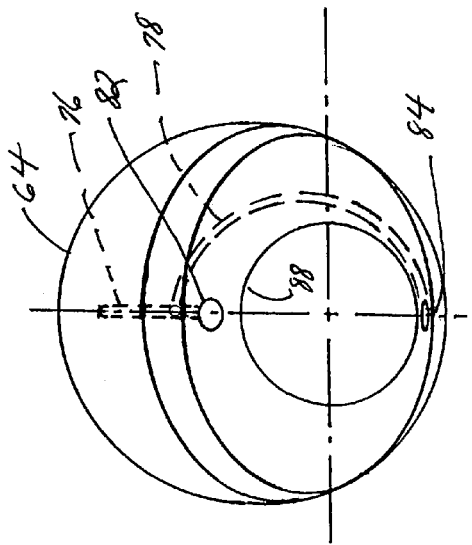
FIG 9
FIG 11
FIG 10

VESSEL HARVESTING APPARATUS

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to apparatus and methods for harvesting of blood vessels and more particularly to an apparatus for separating and removing the sapiens vessel of the leg for use in bypass surgery with minimal tissue trauma.

2. Description of Related Art

Healthy blood vessels are typically harvested to repair damaged vessels in other more critical parts of a human circulatory system. In particular, the sapiens vein is harvested from a patient's leg and utilized in bypass surgery where damaged and blocked arteries of the heart region of the patient are bypassed with the healthy blood vessel harvested.

Typically, the surgeon will harvest an appropriate length of the leg vessel requiring that the vessel be safely separated from side branch vessels and leg tissue, followed by an appropriate dissection of the end of the harvested vessel. In early surgery of this type, incisions were made along the length of the sapiens vessel to be harvested which was then dissected from the surrounding tissue. More modern surgical techniques have been developed and are utilizing a broad variety of vessel harvesting instruments and apparatus which greatly reduce the trauma to the patient. The following U.S. Patents appear to represent at least a substantial portion of this more modern vessel harvesting technology.

U.S. Pat. No. 6,660,016 to Linda discloses an endoscope apparatus for harvesting blood vessels including an endoscope barrel with a plurality of lumens, a handle disposed at a proximal end of the barrel and at lest one member for dissecting and cauterizing a blood vessel. An invention related to devices and methods for removing veins is taught by Spit in U.S. Pat. No. 6,352,544.

David, et al., in U.S. Pat. No. 6,241,740 teaches a system and medical device for endoscopically ligating and cutting a body vessel, the improvements including a hinged jaw, an improved delivery system of a ligating clip and a rotating cutting instrument. A surgical instrument comprising an elongated hollow shaft having a longitudinal axis, a lumen, and an optical penetrating tip having a cylindrical portion attached to the distal end of the hollow shaft is taught by Kolata, et al. in U.S. Pat. No. 6,206,823.

U.S. Pat. No. 6,193,653 to Evans, et al. discloses methods and devices for harvesting vessels comprising a shaft having a handle mounted on one end and a dissecting tip on the other end. A light source is further optionally included and methods for transilluminating a vessel, dissecting the vessel, transecting the vessel and removing the vessel from the body are disclosed.

A method and apparatus for the minimally invasive harvesting of veins is taught by Ginn, et al. in U.S. Pat. No. 6,022,313 and devices and methods for minimally invasive harvesting of a vessel are shown in U.S. Pat. No. 5,913,866. U.S. Pat. No. 6,019,771 to Bennett, et al. teaches similar devices and methods as Ginn, et al. and we note that these three patents have been assigned to Cardiothoracic Systems, Inc.

U.S. Published Application US2005/0070940 to Genovesi, et al. teaches a method and device for harvesting vessels comprising a cannula-like device including means for identification, capture, manipulation, hemostasis and cleavage of branch vessels. That published application is a continuation application of U.S. Pat. No. 6,818,003 directed to a method and device for harvesting vessels. The harvesting cannula is configured as an elongated, hollow tube and comprised of three sections: a harvesting head, a tubular control segment and a sliding operation arm.

Another published application to Hess, et al., US 2003/0065348 and U.S. Pat. No. 6,656,176, disclose endoscope vessel harvesting devices and methods. The method comprises locating the vessel, inserting the device through an incision, dissecting the vessel from the surrounding tissue and capturing vessels. The device comprises a headpiece having electrodes for ligation, a shaft having a lumen, and a vessel capturing means.

Other published applications and issued patents are known to applicant as follows:

U.S. Pat. No. 6,527,786 to Davis, et al.
U.S. Pat. No. 6,679,892 to Guido, et al.
U.S. Pat. No. 6,464,708 to Higuma, et al.
U.S. Pat. No. 6,464,685 to Suzuki, et al.
U.S. Pat. No. 5,695,514 to Chin
U.S. Pat. No. 5,569,291 to Pirvitera, et al.
U.S. Pat. No. 6,004,335 to Vaitekunas, et al.
U.S. Pat. No. 6,375,635 to Moutafis, et al.
U.S. Pat. No. 6,214,028 to Yoon, et al.
U.S. Pat. No. 6,149,659 to Ahmed
U.S. Pat. No. 6,143,005 to Yoon, et al.
U.S. Pat. No. 6,099,535 to Lamport, et al.
U.S. Pat. No. 6,074,402 to Peifer, et al.
U.S. Pat. No. 6,007,551 to Peifer, et al.
U.S. Pat. No. 6,730,101 to Peifer, et al.
U.S. Pat. No. 6,565,578 to Peifer, et al.
U.S. Pat. No. 6,685,713 to Ahmed
U.S. Pat. No. 6,610,072 to Christy, et al.
U.S. Pat. No. 6,632,228 to Fortier, et al.
U.S. Pat. No. 6,607,542 to Wild
U.S. Publ. US2004/0122458 to Opie, et al.
U.S. Publ. US2005/0004586 to Suval
U.S. Publ. US2004/0204725 to Bayer
U.S. Publ. US2005/0096677 to Wellman, et al.

BRIEF SUMMARY OF THE INVENTION

This invention is directed to a vessel harvesting apparatus including a shaft and a tip preferably formed as a unit with, and positioned at a distal end of, the shaft. A handle is connected to a proximal end of the shaft for allowing an operator to feed and manipulate the tip. The tip defines a vessel receiving aperture extending longitudinally through the tip and being laterally offset from and generally parallel to a longitudinal axis of the shaft. The tip has a smooth, contoured outer surface narrowing toward the distal end thereof wherein the tip may be passed along and surrounding a vessel without substantial disruption of surrounding tissue. Transecting and ligating of the vessel positioned in the aperture and side branch vessels against the outer surface of the tip by dissection and/or cauterization is provided. The tip releases the vessel from surrounding tissue while being moved there along wherein the transfected portion of the vessel is more easily removed from surrounding tissue.

It is therefore an object of this invention to provide an improved vessel harvesting apparatus which effectively releases and removes a vessel segment to be harvested from human tissue with minimal trauma to the patient.

Still another object of this invention is to provide for an array of vessel transecting and ligating structures for the efficient dissection of side branch vessels and for the transecting of the harvested vessel from the remaining vessel and surrounding tissue.

Yet another object of this invention is to provide an apparatus for harvesting vessels for use in subsequent surgical repair of a patient's circulatory system which involves a single pass along the harvested vessel and which incorporates all of the necessary functions for vessel removal.

And still another object of this invention is to provide an apparatus for vessel harvesting which minimizes trauma to adjacent tissue and typically requires only a single pass to prepare the vessel for harvesting.

In accordance with these and other objects which will become apparent hereinafter, the instant invention will now be described with reference to the accompanying drawings.

BRIEF DESCRIPTION OF THE SEVERAL VIEWS OF THE DRAWING(S)

FIG. 1 is a side elevation view of one embodiment of the invention in relation to a harvested vessel and a side branch vessel in phantom.

FIG. 2 is an end elevation view showing the tip of FIG. 1.

FIG. 3 is an enlarged side elevation broken view of the tip portion of FIG. 1.

FIG. 6 is an end view of one embodiment of a segmented openable tip.

FIG. 7 is a side elevation view of FIG. 6.

FIG. 8 is an end elevation view of another embodiment of a segmented openable tip.

FIG. 9 is a side elevation view of still another embodiment of the invention.

FIG. 10 is an end elevation view of the tip of FIG. 9.

FIG. 11 is an enlarged side elevation view of the tip of FIG. 9.

DETAILED DESCRIPTION OF THE INVENTION

Figure 4:
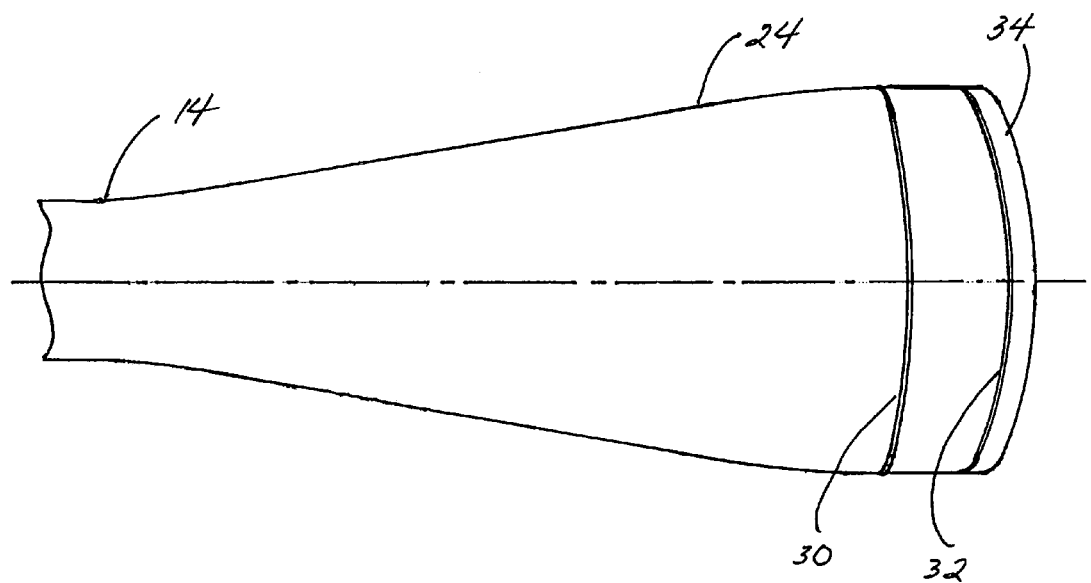
FIG. 4 is a top plan view of FIG. 3.

Referring now to the drawings, and firstly to FIGS. 1 to 5, one embodiment of the invention is there shown generally at numeral 10 in FIG. 1. This vessel harvesting apparatus 10 includes a vessel harvesting device 12 formed as a unit including an elongated slender shaft 14, a laterally extending handle 16 connected and molded as a unit to the proximal end of shaft 14 and a generally barrel-shaped or enlarged and smoothly tapering tip 24.

The elongated shaft 14 may be solid or hollow in cross section and of sufficient stiffness and rigidity to allow the tip 24 to be manipulated and moved along within the patient's body tissue in order to harvest a blood vessel for use in other surgery such as bypass surgery.

Figure 5:
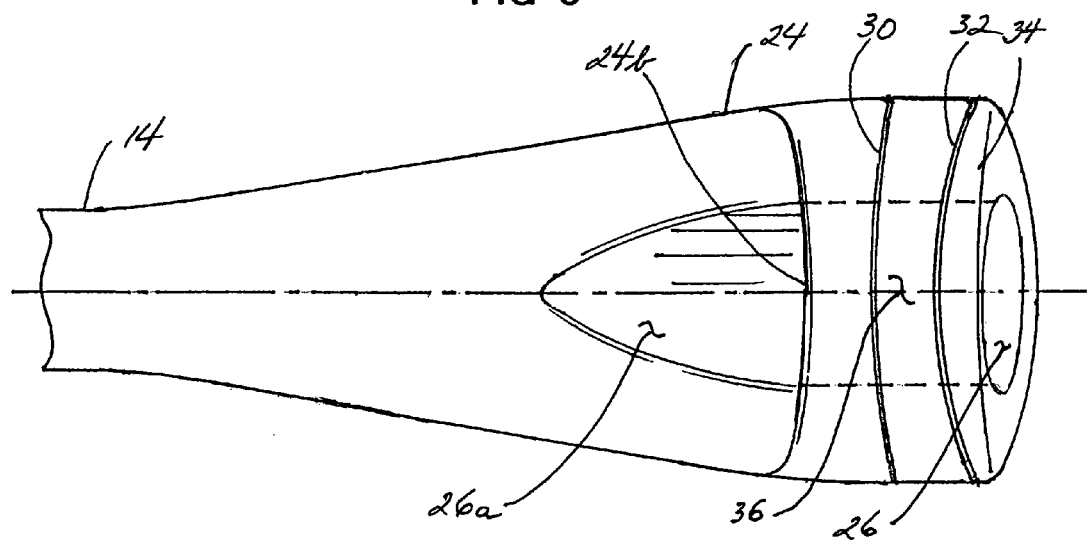
FIG. 5 is a bottom plan view of FIG. 3.

The tip 24 may be characterized in shape and configuration as that of a barrel or having of a tapering smooth bullet-shaped outer surface which is enlarged in lateral dimension and over a relatively short length of the shaft 14 as best seen in FIGS. 3, 4 and 5 with respect to the shaft 14. A typical transverse size ratio between the tip 24 and the shaft 14 is in the range of about 2-3:1. This enlarged lateral configuration of the tip 24 serves to enhance vessel separation from adjacent tissue as described more fully herebelow. The smooth gradual transition between the larger tip 24 and the shaft 14 also reduces the drag of the narrower shaft 14 and the force necessary to move the tip 24 along and around the harvested vessel C.

An elongated cylindrical aperture 26 is formed longitudinally through the tip 24 about an axis 28 which is generally parallel to the length of the shaft 14 and laterally offset therefrom as distance Z as best seen in FIGS. 1 and 3 which is preferably 1-2 times the thickness of the shaft. The aperture 26 is sized so as to be slidably moved over and along the vessel C shown in FIG. 1 to be harvested. A range of diameters or transverse sizes of the aperture 26 may be provided and made available for the surgeon to select from at the time of surgery depending upon the transverse size of the harvested vessel C. Note the smooth contoured outer surface of the tip 24 broadly blending from the shaft 14 and uniformly terminating at radius 34.

In well-known fashion, the vessel harvesting procedure will typically begin with the forming of an incision at the distal aspect of the vessel, including transecting the to-be-harvested vessel. Thereafter, the tip 24 is guided over the to-be-harvested vessel C in FIG. 1 by manipulation thereof by handle 16. The vessel harvesting proceeds by generally axial movement of the device 12 in the direction of the arrow with respect to the harvested vessel C. The shape of the tip 24 is ideal for the gentle release of the vessel C from adjacent tissue without excessive trauma to that support tissue.

Two spaced apart bi-polar cauterizing members or rings 30 and 32 are molded as a unit into the tip 24 having an exposed outer surface thereof in smooth uninterrupted continuity with respect to the outer surface of the tip 24. Conductive wires 20 and 22 extend through the shaft 14 and handle 16 to connector 18 which exteriorly connects to a suitable electric power source +/− V. This voltage source is sufficient to implement a bi-polar cautery environment between the cautery bands 30 and 32 at 38a and 38b. These cautery rings 30 and 32 extend circumferentially around virtually the entire tip 24 such that, as seen in FIG. 1, when a side branch vessel P or R of the vessel to be harvested C is encountered by the tip 24, the surgeon will then apply an appropriate voltage producing sufficient cauterizing heat in the regions 38a and 38b to cauterize, transect and ligate the side branch vessels P and R at regions O and S, respectively in one operation.

Referring briefly to FIG. 5, the longitudinal aperture 26 is blended at the proximal end thereof at 26a in bullet-shaped fashion to accommodate the tapered proximal surface 24b of tip 24. In similar fashion, the distal end of the aperture 26 is blended to accommodate an inclined distal end 24a, both features of which decrease the force necessary to separate the harvested vessel from surrounding tissue and thus reduce the overall trauma associated with this portion of a typical vessel harvesting surgical procedure.

Referring now to FIGS. 6, 7 and 8, an alternate embodiment of the tip is there shown at 24c at the distal end of shaft 14a. This tip 24c includes openable tip segments 44 and 46 which are hingedly connected along longitudinal hinges 40 and 42 such that the tip segments 44 and 46 are openable in the direction of arrow A to be inserted around the harvested vessel without the initial requirement of dissecting the vessel first. These tip segments 44 and 46 meet at 48 such that the aperture 24b remains substantially cylindrical to avoid damaging or excessive rubbing of the vessel to be harvested.

In FIG. 8, the lower tip segment 54 is formed of a single piece pivotally connected along a single longitudinal hinge 52, the lower tip segment 54 being openable in the direction of arrow B and closeable around the vessel at 56 so as to maintain the interior smoothness and uninterrupted nature of the longitudinal aperture 26c.

Referring now to FIGS. 9, 10 and 11, another embodiment of the vessel harvesting apparatus is there shown generally at numeral 60 and includes the molded harvesting device 62 formed to include an elongated shaft 64, a molded handle 66 and a molded tip 80. In this embodiment 62, the handle 66 is made rotatably adjustable with respect to the tip 80 by a releasable rotating joint 74 such that, as seen in phantom, the handle 66 may be oriented at any desired different radial angle with respect to the tip 80 as desired during the surgical procedure.

A variety of lumens or internal passageways 76 and 78 are provided within the shaft 64 which, again may be tubular in nature or molded to have a substantially filled cross section. These lumens 76 and 78 extend beyond the distal end of the shaft 64 and terminate, for example, at 82, 84 and 86 strategically located with respect to the configuration of the tip 80 and the longitudinal aperture 88. The lumens 76 and 78 accommodate and position ancillary surgical accessories such as an endoscope attached at the proximal end of the shaft 64 to a camera 70, or to camera tips located at 82 and 84 with appropriate wires 76 and 78, or to a gas source of $CO_2$ or $O_2$ insufflations. Thus, as desired, the function of additional lighting, an optical endoscope function, and/or the addition of selected gas at the current exact point of release of the harvested vessel from adjacent tissue may also be provided. These ancillary functions may be supported by a small battery 72 housed within the handle 66 which may be hollowed for that purpose.

Figure 13:
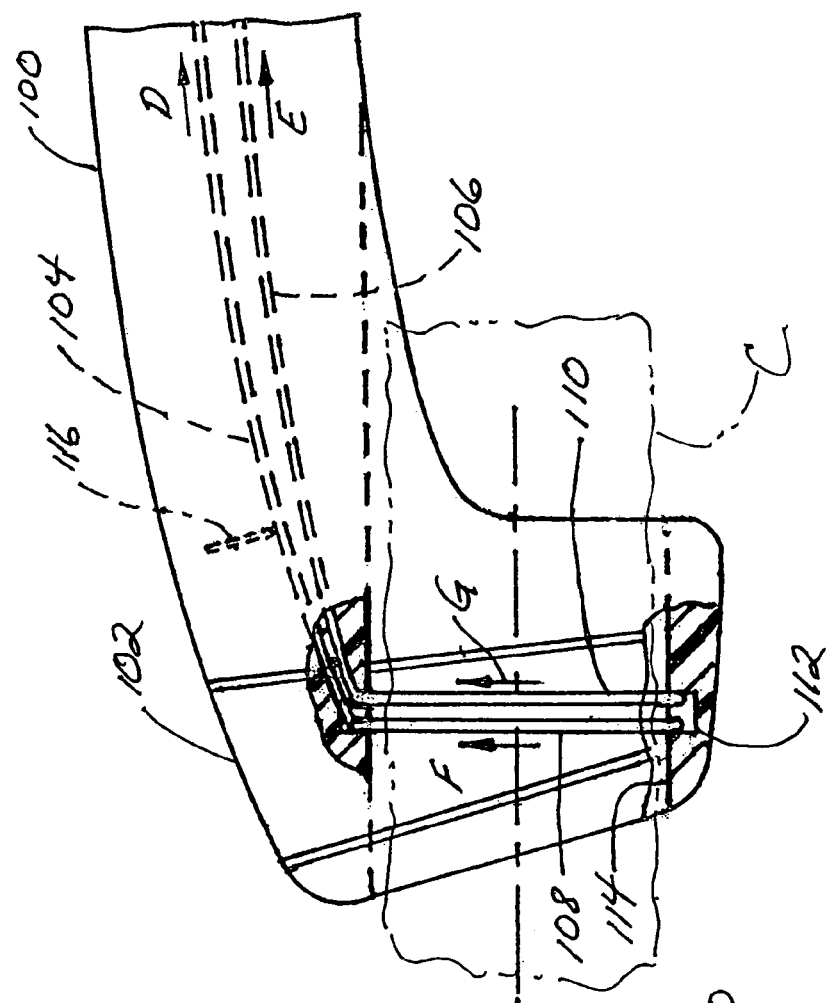
FIG. 13 is a side elevation view of FIG. 12.
Figure 12:
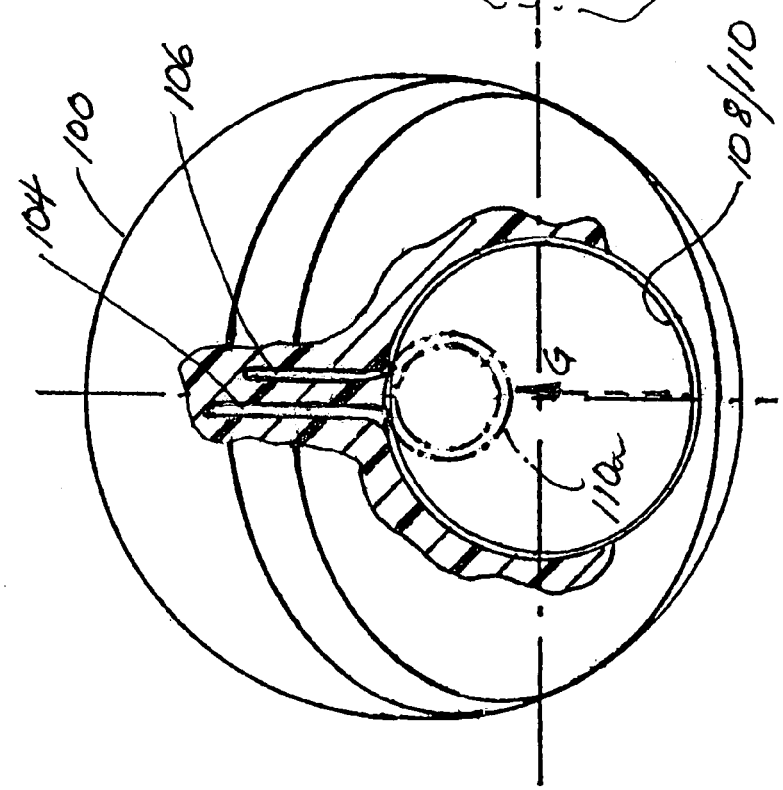
FIG. 12 is an end elevation view of yet another embodiment of the tip showing a vessel transecting loop in the closed position in phantom.

Referring now to FIGS. 12 and 13, another embodiment of the shaft 100 and tip 102 is there shown. In this embodiment of the tip 102, the function of transecting and ligating the harvested vessel is there shown. A looped ligation suture 108 and a metal transecting wire snare 110 are nested in side-by-side relationship within an annular groove 112 formed into the cylindrical surface of the longitudinal aperture 114. After the tip 102 has been moved along the harvested vessel shown in phantom at C a distance sufficient to produce a desired vessel length to be harvested, the loop of suture 108 is pulled taught by the suture extension 104 which extends outwardly from the handle (not shown). The suture may then be clipped by a heat cutting blade 116 or other suitable suture cutting mechanism. Thereafter, the extension of the metal wire snare 110 is pulled in the direction of arrow E which extends again through the handle (not shown) of this embodiment 100 thus reducing the diameter of the wire snare 110 into an approximate configuration shown in phantom in FIG. 12 at 110a which moves upwardly in the direction of arrow G. At any size in this size range shown in phantom in FIG. 12, the metal wire snare 110a is sufficiently small to have transfected the vessel C and suture 108 leaving the tightened suture knot 108 in place around the transfected end of the vessel remaining within the tissue.

Figures 14, 15:
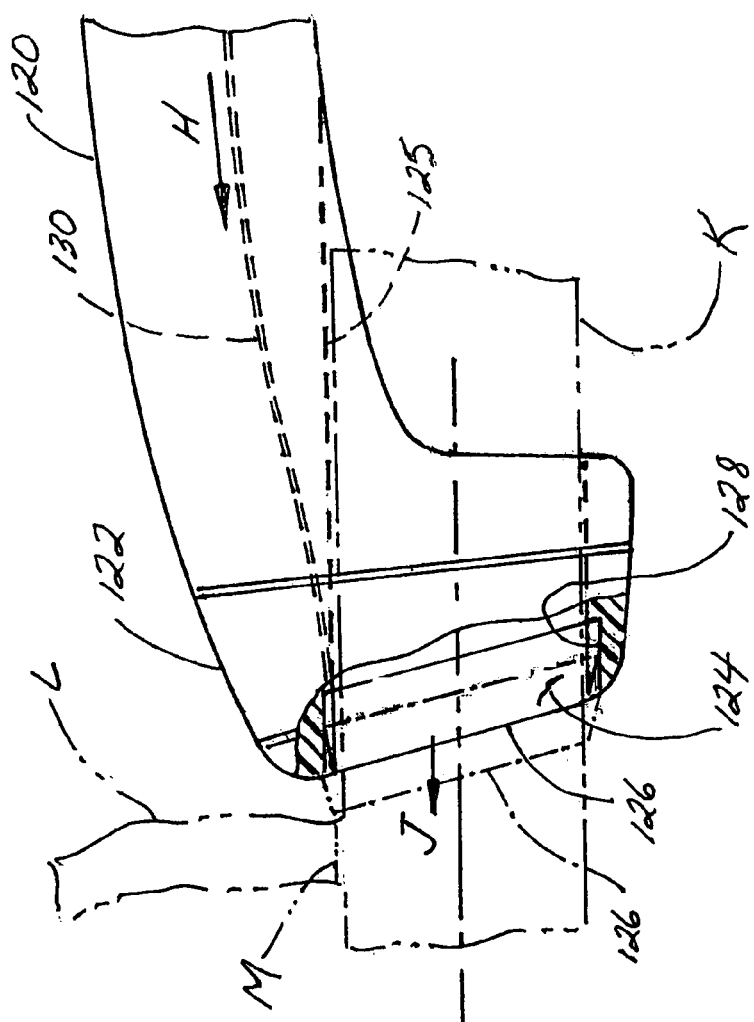
FIG. 14 is an end elevation view of yet another embodiment of the tip.
FIG. 15 is a side elevation view of FIG. 14 showing the vessel and the side branch vessel in phantom.

In FIGS. 14 and 15, one method of disconnecting side branch vessels at L from the harvested vessel K shown in phantom is provided. This branch vessel truncation is accomplished by the exposure in the direction of arrow J of a circular or ring-shaped knife 124 which, when stored, is positioned within a continuous groove 128 formed into the distal end of the longitudinal aperture 125. When the knife ring 124 is extended longitudinally as shown in phantom in the direction of arrow J by pushing on a control wire H, the proximal end of which is extended from the handle (not shown), the cutting edge 126 is exposed. By slight rotational movement of the knife edge 126 by handle movement, transection of the side branch vessel L is accomplished at cut line M.

Figure 16:
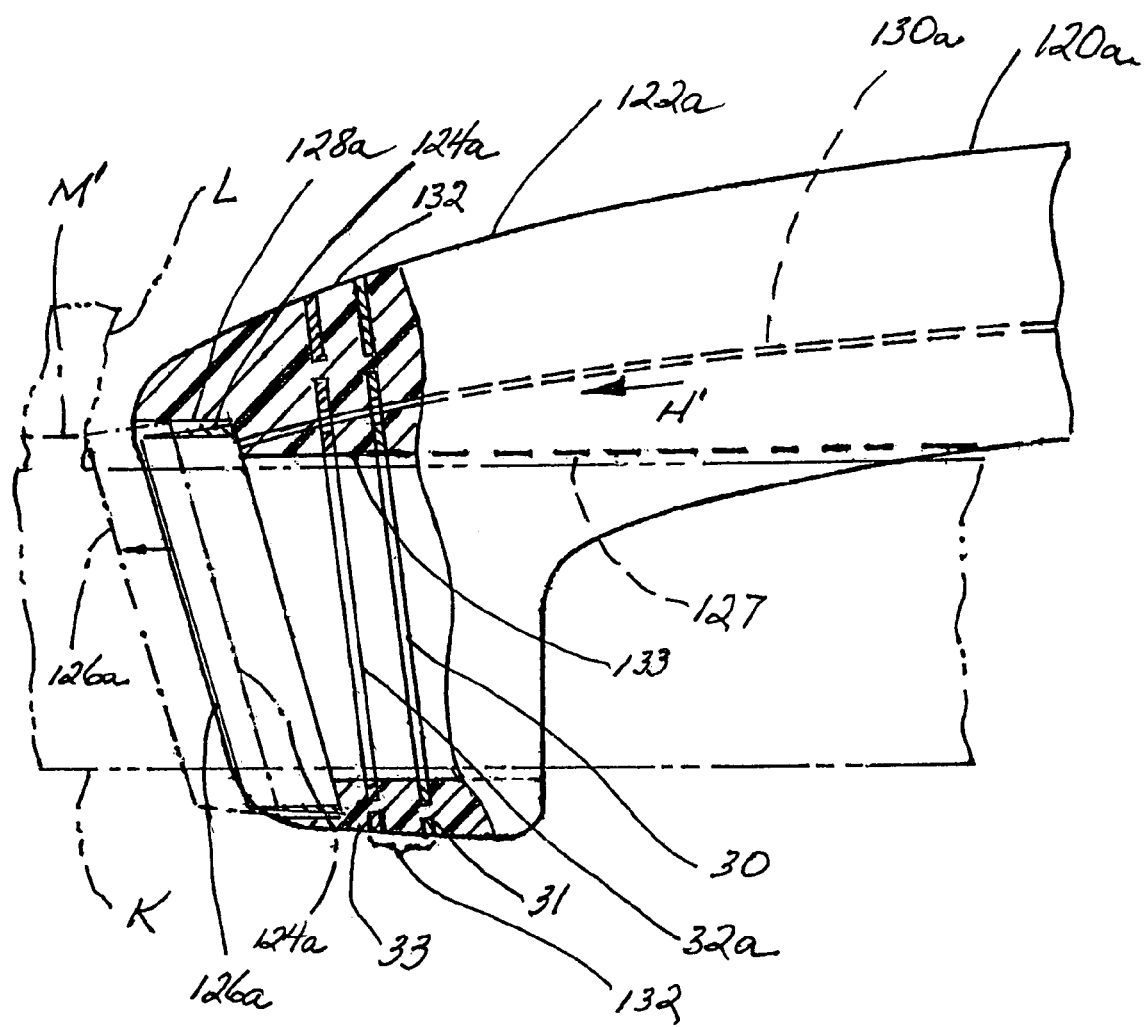
FIG. 16 is an enlarged side elevation broken view of yet another embodiment of the tip and also showing the harvested vessel and the side branch vessel in phantom.

Referring now to FIG. 16, alternate embodiments for (a) the cauterizer of the harvested vessel K, (b) cutting transection and (c) heat cauterization of the side branch vessel L are there shown. The tip 122a includes the previously described knife ring 124a which is slightly enlarged in diameter and snugly fits within the mating circular-spiral cavity 128a such that the cutting edge 126a is fully within the distal end surface of the tip 122a when not in use. When a side branch vessel L is encountered, the knife ring 124a is extended such that the cutting edge 126a is pressed against and will transect the side branch vessel A at cut line M'. Note that the diameter of the knife ring 124a is enlarged so that a larger vessel stump remains attached to the harvested vessel K to facilitate suture closure thereof after the vessel K is removed.

Cauterization, which accomplishes both transection and ligation in one operation, is provided in this tip embodiment 122a with respect to both the harvested vessel K and any side branch vessel shown typically at L. There are two pairs of cauterization rings, the outer cauterizing rings 31 and 33 and the inner cauterization rings 30 and 32a. The outer cauterizing rings 31 and 33 are spaced apart a distance at 132 which is uniform around the entire circumference or periphery of the tip 122a so that the heat factor for cauterization is thereby uniform in all directions and positions on the outer surface of the tip 122a. Thus, when the side branch vessel L lays across and between the outer cauterizing rings 131 and 133, cauterization, transection and ligation in the region 132 are accomplished. To cauterize and transect the vessel K, the inner cauterizing rings 130 and 132a may be selectively energized by electric power (not shown) so that cauterization of the vessel K occurs at 133 around the entire circumference of the vessel K.

Figure 17:
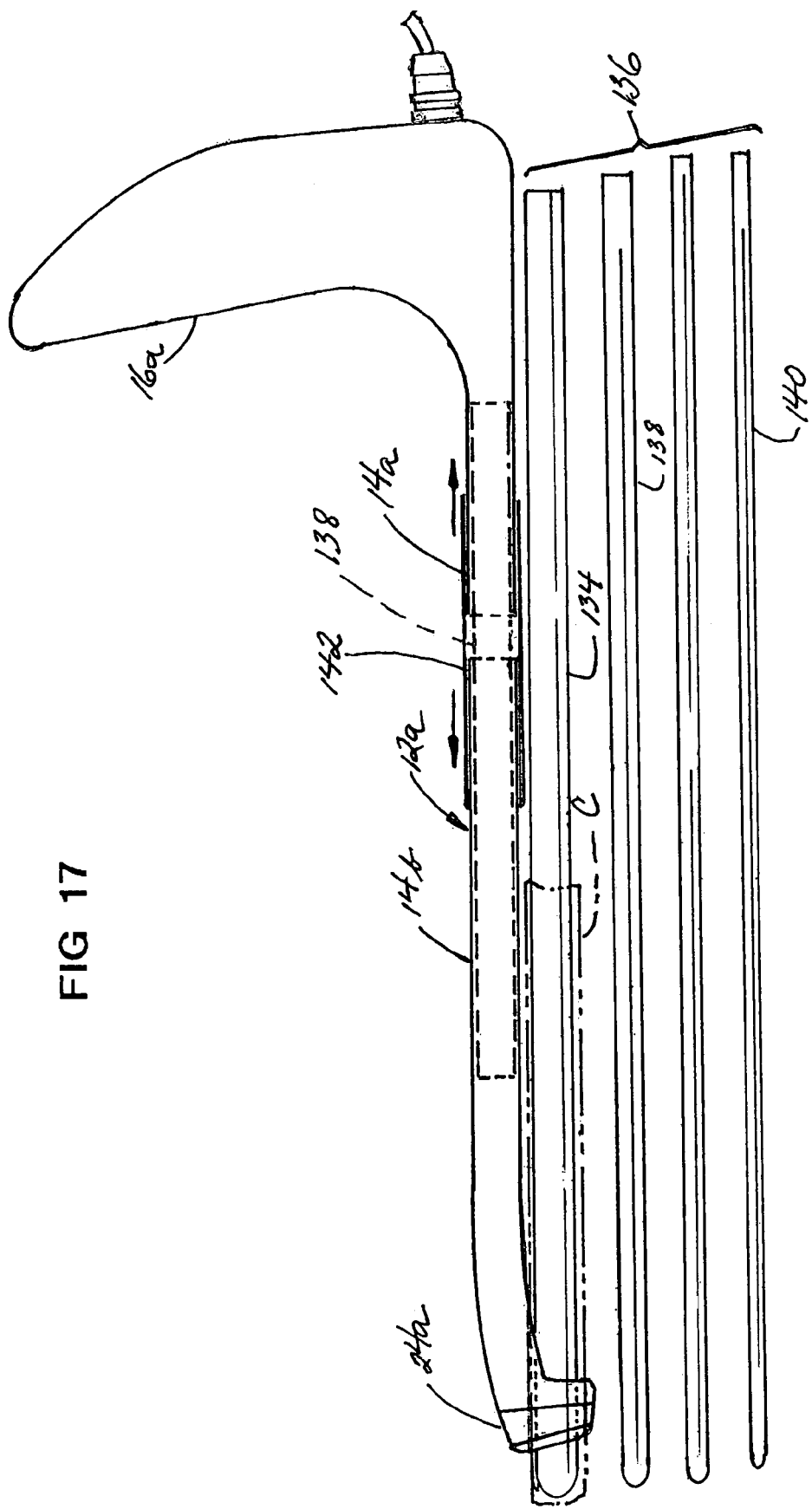
FIG. 17 is a side elevation view of still another embodiment of the invention showing the addition of elongated branch vessel support rods, one of which is shown inserted into a vessel shown in phantom.

Lastly in FIG. 17, an alternate embodiment of the entire device is shown at 12a and includes a molded handle 16a which is rotatably positionable with respect to the tip 24a on shaft portion 12a. An elongated tubular splicing member 138 is tightly but forcibly movably positioned within the tubular portions of each of the shaft sections 14a and 14b such that the shaft sections 14a and 14b are also extendable in the direction of the arrows. A very thin sheath 142 covers the exposed portion of the splicing member 138 and the gap between the ends of the shaft 14*a* and 14*b* so as to minimize any tissue disruption as the shaft, led by the tip 24*a*, passes through the tissue and along and around the periphery and side walls of the vessel to be harvested.

To support harvested vessels which may be weakened or lack sufficient side wall integrity to undergo harvesting as above described, support rods 134, 138 and 140 are provided in different diameters and are selected depending upon the size of the vessel C to be harvested. The array of vessel support members shown at 136 would be available at the time of surgery and the particular diameter or transverse size of the vessel support member 134, 138 or 140 would be selected. It is anticipated that these diameters would be in the range of 2 mm to 10 mm in diameter.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. A vessel harvesting apparatus comprising:
    an elongated slender shaft and an enlarged tip formed as a unit with, and positioned at a distal end of, said shaft;
    a handle connected to, and laterally extending from a proximal end of, said shaft for allowing an operator to feed and manipulate said tip over and along a vessel;
    said tip including a vessel receiving aperture extending substantially longitudinally through said tip, said aperture having a longitudinal axis which is laterally offset from a longitudinal axis of said shaft, said tip having a smooth, contoured substantially uninterrupted outer surface gradually and smoothly narrowing toward a distal end of said tip and terminating at a substantially uniform radius around the axis of said aperture, wherein said tip may be passed along a vessel with the vessel positioned within said aperture without substantial disruption of surrounding tissue;
    means for transecting and ligating the vessel positioned in said aperture;
    means for transecting and ligating side branch vessels extending laterally from the vessel;
    said tip releasing the vessel from surrounding tissue while being moved therealong wherein a transfected portion of the vessel is more easily removed from surrounding tissue.

2. A vessel harvesting apparatus as set forth in claim 1, wherein:
    said means for transecting and ligating the vessel is a cauterizing member.

3. A vessel harvesting apparatus as set forth in claim 2, wherein:
    said cauterizing member includes spaced cauterization bands extending substantially circumferentially around an outer surface of said tip, said bands being in electrical communication with an electric power source wherein said bands produce sufficient heat therebetween to transect and cauterize each side branch vessel becoming positioned across said bands as said tip is moved along the vessel.

4. A vessel harvesting apparatus as set forth in claim 2, wherein:
    said cauterizing member includes spaced cauterization bands extending substantially circumferentially around an interior wall surface of said aperture, said bands being in electrical communication with an electric power source wherein said bands produce sufficient heat therebetween to transect and cauterize the vessel within said aperture.

5. A vessel harvesting apparatus as set forth in claim 2, wherein:
    said cauterizing member includes a pair of spaced first cauterization bands extending substantially Circumferentially around an outer surface of said tip and a pair of spaced second cauterization bands extending substantially circumferentially around an interior wall surface of said aperture and in electrical communication with an electric power source, said first and second bands selectively producing sufficient heat therebetween on said outer surface of said tip or said interior surface of said aperture to transect and cauterize a side branch vessel positioned against the outer surface of said tip or within said aperture, respectively.

6. A vessel harvesting apparatus as set forth in claim 1, wherein:
    said means for transecting and ligating the vessel includes a reducible in diameter wire loop and a tensionable suture loop, respectively, said loops being positioned circumferentially around an interior wall surface of said aperture.

7. A vessel harvesting apparatus as set forth in claim 1, wherein:
    said means for transecting side branch vessels includes a substantially continuous ring knife extending circumferentially around a distal end of said aperture, said ring knife extendable longitudinally from said distal end to transect side branch vessels positioned thereagainst as said tip is manually moved along the vessel and rotated back and forth.

8. A vessel harvesting apparatus as set forth in claim 1, further comprising:
    an elongated vessel support rod sized in width to be slid into, and to provide support for, the vessel as said tip is passed over and along the vessel.

9. A vessel harvesting apparatus as set forth in claim 8. wherein:
    said handle extends laterally from said shaft in a different direction from that of said tip wherein said support rod positioned in the vessel does not contact said handle as said tip is moved along the vessel.

10. A vessel harvesting apparatus as set forth in claim 1, wherein:
    said aperture is segmented along a longitudinally extending hinge wherein said aperture is openable for lateral engagement around the vessel.

11. A vessel harvesting apparatus as set forth in claim 1, further comprising:
    a lumen, an endoscope or a $CO_2$ discharge port operably connected into said tip.

12. A vessel harvesting apparatus as set forth in claim 11, wherein:
    shaft is telescopically variable in length;
    said handle is radially rotatable with respect to said tip for enhanced manual manipulation of said tip passing along the vessel.

13. A vessel harvesting apparatus comprising:
    an elongated slender shaft and an enlarged tip formed as a unit with, and positioned at a distal end of, said shaft;
    a handle connected to, and laterally extending from a proximal end of, said shaft for allowing an operator to feed and manipulate said tip along the vessel;

said tip including a vessel receiving aperture extending substantially longitudinally through said tip, said aperture having a longitudinal axis which is laterally offset from a longitudinal axis of said shaft wherein the vessel is positioned in close proximity against said shaft, said tip having a smooth, contoured barrel-shaped substantially uninterrupted outer surface narrowing toward a distal end of said tip and terminating at a substantially uniform radius around the axis of said aperture, wherein said tip may be passed along a vessel with the vessel positioned within said aperture without substantial disruption of surrounding tissue;

a transecting and ligating member for transecting and ligating the vessel positioned in said aperture;

a transecting member for transecting side branch vessels extending laterally from the vessel;

said tip releasing the vessel from surrounding tissue while being moved therealong wherein a transfected portion of the vessel is more easily removed from surrounding tissue.

14. A vessel harvesting apparatus comprising:

an elongated slender shaft and an enlarged tip formed as a unit with, and positioned at a distal end of, said shaft;

a handle connected to and laterally extending from a proximal end of said shaft, for allowing an operator to feed and manipulate said tip into an incision made in leg tissue and along a sapiens vessel;

said tip including a vessel receiving aperture extending substantially longitudinally through said tip, said aperture having a longitudinal axis substantially parallel to and laterally offset from a longitudinal axis of said shaft, said tip having a smooth, contoured substantially uninterrupted outer surface gradually transitioning and narrowing toward a distal end of said tip and terminating at a substantially uniform radius around the axis of said aperture wherein said tip may be passed along the vessel positioned within said aperture without substantial disruption of surrounding tissue;

means for transacting and ligating the vessel positioned in said aperture;

means for transecting and ligating branch vessels extending laterally from the vessel;

said tip releasing the vessel from surrounding tissue while being moved therealong wherein the transfected portion of the vessel is more easily removed from surrounding tissue.

15. A vessel harvesting apparatus as set forth in claim 14, wherein:

said means for transacting and ligating the vessel is a cauterizing member.

16. A vessel harvesting apparatus as set forth in claim 15, wherein:

said cauterizing member includes spaced cauterization bands extending substantially circumferentially around an outer surface of said tip, said bands being in electrical communication with an electric power source wherein said bands produce sufficient heat therebetween to transect and cauterize each side branch vessel becoming positioned across said bands as said tip is moved along the vessel.

17. A vessel harvesting apparatus as set forth in claim 15, wherein:

said cauterizing member includes spaced cauterization bands extending substantially circumferentially around an interior wall surface of said aperture, said bands being in electrical communication with an electric power source wherein said bands produce sufficient heat therebetween to transect and cauterize the vessel within said aperture.

18. A vessel harvesting apparatus as set forth in claim 15, wherein:

said cauterizing member includes a pair of spaced first cauterization bands extending substantially circumferentially around an outer surface of said tip and a pair of spaced second cauterization bands extending substantially circumferentially around an interior wall surface of said aperture and in electrical communication with an electric power source, said first and second bands selectively producing sufficient heat therebetween on said outer surface of said tip or said interior surface of said aperture to transect and cauterize a side branch vessel positioned against the outer surface of said tip or within said aperture, respectively.

19. A vessel harvesting apparatus as set forth in claim 14, wherein:

said means for transecting and ligating the vessel includes a reducible in diameter wire loop and a tensionable suture loop, respectively, said loops being positioned circumferentially around an interior wall surface of said aperture.

20. A vessel harvesting apparatus as set forth in claim 14, wherein:

said means for transecting side branch vessels includes a substantially continuous ring knife extending circumferentially around a distal end of said aperture, said ring knife extendable longitudinally from said distal end to transect side branch vessels positioned thereagainst as said tip is manually moved along the vessel and rotated back and forth.

21. A vessel harvesting apparatus as set forth in claim 14, further comprising:

an elongated vessel support rod sized in width to be slid into, and to provide support for, the vessel as said tip is passed over and along the vessel.

22. A vessel harvesting apparatus as set forth in claim 21, wherein:

said handle extends laterally from said shaft in a different direction from that of said tip wherein said support rod positioned in the vessel does not contact said handle as said tip is moved along the vessel.

23. A vessel harvesting apparatus as set forth in claim 14, wherein:

said aperture is segmented along a longitudinally extending hinge wherein said aperture is openable for lateral engagement around the vessel.

24. A vessel harvesting apparatus as set forth in claim 14, further comprising:

a lumen, an endoscope, camera tips or a $CO_2$ discharge port operably connected into said tip.

25. A vessel harvesting apparatus as set forth in claim 24, wherein:

shaft is telescopically variable in length;

said handle is radially rotatable with respect to said tip for enhanced manual manipulation of said tip passing along the vessel.

* * * * *